Figure 1A:
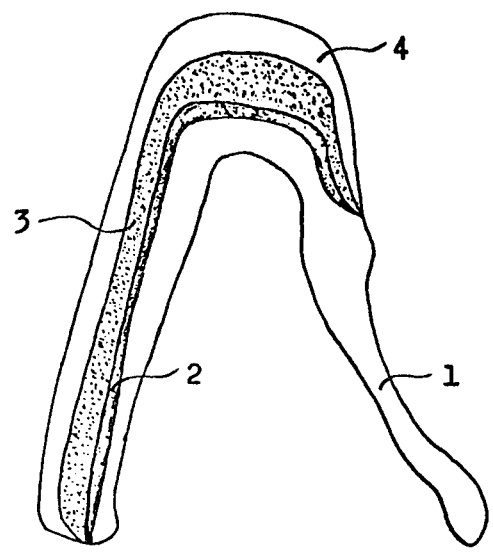

United States Patent [19]

Takahashi et al.

[11] 4,104,798

[45] Aug. 8, 1978

[54] PORCELAIN FUSED TO METAL CROWN

[75] Inventors: Shigeo Takahashi; Michio Ito, both of Shioziri, Japan

[73] Assignees: Sumitomo Chemical Company, Limited, Osaka; Matsumoto Dental College, Shioziri, both of Japan

[21] Appl. No.: 707,715

[22] Filed: Jul. 21, 1976

[30] Foreign Application Priority Data

Jul. 21, 1975 [JP] Japan ................................ 50-89541
Jul. 22, 1975 [JP] Japan ................................ 50-89781

[51] Int. Cl.² ............................................. A61C 5/08
[52] U.S. Cl. ...................................................... 32/12
[58] Field of Search ................................. 32/12, 8, 2

[56] References Cited

U.S. PATENT DOCUMENTS 3,069,773  12/1962  Soffir ........................................ 32/8
3,423,829  1/1969  Halpern et al. ........................... 32/8

Primary Examiner—Robert Peshock
Attorney, Agent, or Firm—Birch, Stewart, Kolasch and Birch

[57] ABSTRACT

An improved porcelain fused to metal crown having a composite structure comprising layers of a bonding agent and ceramics and optionally a mixture of a bonding agent and ceramics and/or a mixture of ceramics and a porcelain, which are thermally sprayed around the metal crown, and a layer of fused porcelain formed on the above layers. The porcelain fused to the metal crown is useful for restoration of a defective tooth crown as an artificial tooth crown.

13 Claims, 4 Drawing Figures

PORCELAIN FUSED TO METAL CROWN

BACKGROUND OF THE INVENTION

The present invention relates to an improved porcelain fused to metal crown which is useful for an artificial tooth crown in the restoration of a tooth crown.

When the tooth crown is partially or wholly lost owing to various diseases, such as dental caries and paradental disease, traffic accidents or the like, the defective portion is restored with an artificial material for esthetic purposes and for recovering the mastication function and the utterance function. When the defect of the tooth crown is small, it is remedied by an inlay technique, and when the defect thereof is large, it is remedied by prosthetic dentistry, such as post crown, bridge denture and plate denture.

The enamel portion of natural teeth has a knoop hardness of 300 to 350, and among the dental materials, only porcelain has an excellent hardness comparative with that of natural teeth. Furthermore, porcelain has superior chemical stability and low thermal conductivity and is more preferable from an esthetic viewpoint, such as color and transparency, in comparison with the metallic restorations.

Although porcelain has an excellent compressive strength, it is inferior in tensile strength and shearing force. In about 1950, a porcelain fused to metal crown was developed in The United States of America. The porcelain fused to metal crown has both characteristics of excellent strength owing to the metal and the excellent esthetic properties similar to natural teeth and excellent wear resistance owing to the porcelain, by which the brittleness of the porcelain is complemented with the strength of the metal, and therefore, it has been widely used. However, it has still some defects. For instance, the alloys used therefor should have a higher melting point than the baking temperature of porcelain. Moreover, as the metal crown, there have been used the products made of noble metal alloys (e.g. platinum-gold alloy) because of the good compatibility thereof with porcelain, but the metal crown should be subjected to troublesome pretreatments, such as the treatment with hydrofluoric acid and the degassing treatment. They have further defects, such as cracking or breaking of the porcelain layer, which may be owing to the deformation of the crown due to the difference in the thermal expansion coefficient between the metal crown and the porcelain and the mechanically intermeshing pressure.

As the results of the present inventors' extensive studies, it has been found that a porcelain fused to metal crown having a composite structure comprising layers of a bonding agent and ceramics thermally sprayed around the metal crown and a layer of fused porcelain thereon can give an excellent artificial tooth crown excellent mastication properties, and aesthetic requirements and further having superior durability in comparison with the conventional porcelain fused to noble metal crown, even when using cobalt-chromium alloys and nickel-chromium alloys which have hitherto been considered to be difficult in the baking of said alloys onto porcelain. Furthermore, the artificial tooth crown has an excellent bonding strength between the porcelain layer and the metal crown without requiring the degassing treatment and the treatment with hydrofluoric acid even by using noble metal alloys as used in the conventional procelain fused to metal crown.

An object of the present invention is to provide an improved porcelain fused to metal crown having a composite structure comprising layers of a bonding agent and ceramics thermally sprayed around the metal crown and a layer of fused porcelain thereon.

Another object of the present invention is to provide an artificial tooth crown having excellent durability, mastication properties and aesthetic requirements.

A further object of the present invention is to provide an artificial tooth crown using cobalt-chromium alloys or nickel-chromium alloys for the metal crown.

A still further object of the present invention is to provide a method for preparing a porcelain fused to metal crown.

Other objects and further scope of applicability of the present invention will become apparent from the detailed description given hereinafter; it should be understood, however, that the detailed description and specific examples, while indicating preferred embodiments of the invention, are given by way of illustration only, since various changes and modifications within the spirit and scope of the invention will become apparent to those skilled in the art feom this detailed description.

In the present specification and claims, the term "porcelain fused to metal crown" denotes an artificial tooth crown, including various types of bridge.

The porcelain fused to metal crown has a composite structure comprising layers of a bonding agent and ceramics, and optionally a mixture of a bonding agent and ceramics, which are thermally sprayed around the metal crown, and a layer of fused porcelain formed on the above layers.

With reference to the accompanying drawings, the porcelain fused to metal crown of the present invention is illustrated.

Figure 1B:
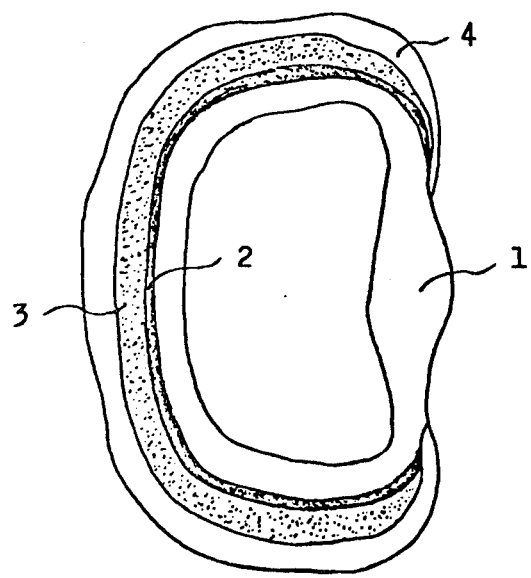

In the drawings,

FIG. 1 shows one embodiment of an artificial tooth crown of the present invention, wherein (A) is a vertical sectional view thereof and (B) is a horizontal sectional view thereof. In FIG. 1, 1 is a metal crown, 2 is a plasma sprayed layer of bonding agent, 3 is a plasma sprayed layer of ceramics, and 4 is a layer of fused and baked porcelain.

Figure 2A:
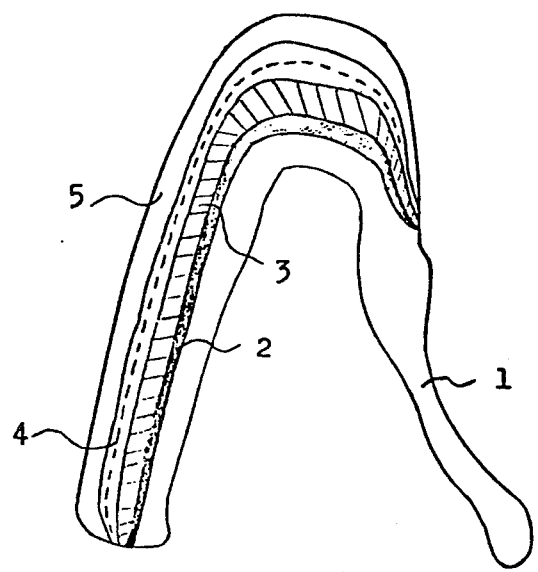
Figure 2B:
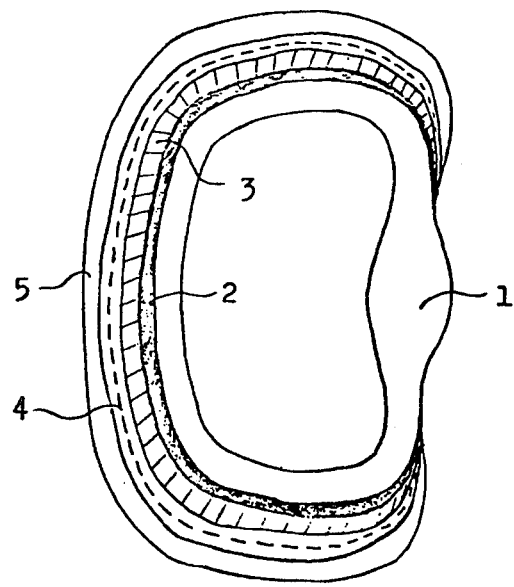

FIG. 2 shows another embodiment of an artificial tooth crown of the present invention, wherein (A) is a vertical sectional view thereof and (B) is a horizontal sectional view thereof. In FIG. 2, 1 is a metal crown, 2 is a plasma sprayed layer of bonding agent, 3 is a plasma sprayed layer of a mixture of ceramics containing zirconium oxide and a bonding agent, 4 is a plasma sprayed layer having pores of a ceramics mixture comprising predominantly zirconium oxide and aluminum oxide, and 5 is a layer of fused and baked porcelain.

According to the present invention, by incorporating zirconium oxide into the thermally sprayed layers 3 and 4 as shown in FIG. 2, the artificial tooth crown having the desired color similar to that of natural teeth can be obtained by a comparatively easy procedure such as coating with a dentin porcelain without the steps for coating with an opaque porcelain and the baking thereof which are essential for sheltering the metallic color in the conventional products and which require a comparatively long processing time. Furthermore, the materials for these steps are expensive.

Particularly, when the mixed ratio of zirconium oxide and aluminum oxide included in the thermally sprayed layer 4 as shown in FIG. 2 is varied, the color of the product may easily be controlled in various ways from white-rich color to a faint yellowish opaque color.

Besides, according to the present invention, when the thermally sprayed layer is formed from a mixture of ceramics and porcelain, the desired excellent artificial teeth can be obtained within a comparatively short time only by coating an enamel porcelain and baking the resultant without the coating of opaque and dentin porcelains.

The materials for the metal crown used in the present invention include dental casting alloys having a melting point of 1,100° C or higher, for instance, base metallic alloys containing 0 to 80% by weight of cobalt, 5 to 70% by weight of chromium and 0 to 90% by weight of nickel and optionally containing further one or more elements selected from the group consisting of iron, molybdenum, silicon, carbon, tungsten, manganese, aluminum, beryllium, magnesium, copper or the like, and noble metallic alloys containing 25 to 95% by weight of gold and optionally further one or more elements selected from the group consisting of silver, platinum, palladium, copper, ruthenium, zinc, iron, indium, tin or the like. Suitable examples of the alloys are cobalt-chromium alloys (e.g. Vitalium ®), cobalt-chromium-nickel alloys (e.g. Ticonium ®), nickel-chromium alloys (e.g. Lunorium ®), iron-cobalt-chromium-nickel alloys (e.g. Dentillium ®), and gold alloys (e.g. KIK ®). The components of these and other suitable alloys are shown in the following Table 1.

a slight amount of ferric oxide ($Fe_2O_3$), chromium dioxide ($CrO_2$) or the like for controlling the color.

The layer of ceramics may be thermally sprayed on the layer of bonding agent in a thickness of not more than 1000 $\mu$, preferably in a range of from 50 to 500 $\mu$. Further, when the layer of a mixture of a bonding agent and ceramics, or a mixture of ceramics and a porcelain is applied on the layer of bonding agent or ceramics, respectively, the thickness of the layer of the mixture of a bonding agent and ceramics is generally not more than 1000 $\mu$, preferably in a range of 50 to 500 $\mu$, and the thickness of the layer of the mixture of ceramics and a porcelain is generally not more than 2000 $\mu$, preferably in a range of from 50 to 1000 $\mu$.

The porcelains used in the present invention include any product having a baking temperature of not more than 1,100° C and being capable of coating, for instance, a mixture and/or a molten salt, which contains predominantly silicon dioxide ($SiO_2$), aluminum oxide ($Al_2O_3$), calcium oxide (CaO), potassium oxide ($K_2O$), sodium oxide ($Na_2O$), zirconium oxide ($ZrO_2$), titanium oxide ($TiO_2$), barium oxide (BaO), boron trioxide ($B_2O_3$), stannic oxide ($SnO_2$), or the like. Suitable examples of the porcelains are the commercially available dental porcelains (opaque, dentin, enamel, or translucent) for baking onto dental metal crowns. Depending on the primary coat (the kind of the thermally sprayed layer), the opaque or opaque-dentin porcelain may be omitted. The opaque porcelain means a material having a higher Table 1

| Name of alloys (trade name) | Components of the alloys (% by weight) | | | | | | | | | | |
|---|---|---|---|---|---|---|---|---|---|---|---|
| | Co | Cr | Ni | Fe | Mo | Si | C | Au | Pt | Pd | Others |
| Vitalium | 61.1 | 31.6 | 0.29 | 0.58 | 4.41 | 0.63 | 0.40 | | | | Mn = 0.71, Al = 0.01 |
| Croform | 64.7 | 27.9 | | 0.6 | 5.7 | 1 | 0.3 | | | | |
| Wisil | 60 | 29 | | | | | | | | | W = 1 |
| Durallium | 62.1 | 31.4 | 0.1 | 0.6 | 5.8 | 0.16 | 0.15 | | | | Mn = 0.68 |
| Springhard | 64.6 | 28.05 | 0.48 | 0.35 | 5.4 | 0.68 | 0.43 | | | | Al = 0.06, Mg = 0.10 |
| Nobilium | 60 | 30 | 1 | | 5 | | | | | | |
| Regalloy | 62.5 | 26.2 | 2.1 | 1.7 | 5.1 | | | | | | |
| Platinore | 60.7 | 26.7 | 2.7 | 2.6 | 5.8 | | | | | | |
| Ticonium | 15.4 | 24.6 | 54.3 | 0.71 | 4.31 | 0.45 | 0.013 | | | | Al = 0.02, Cu = 0.03 |
| Niranium | 46 | 30 | 11 | | 6 | | | | | | W = 8 |
| NIH | 51.6 | 26.7 | 15.5 | | 3.6 | | | | | | |
| Sankolium S | | 10 | 85 | | 5 | | | | | | |
| Dentillium C-B | 8.0 | 28.5 | 6.0 | 46.0 | | | | | | | |
| Dentillium P-D | 6.0 | 24.0 | 4.0 | 63.3 | | | | | | | |
| Wiron-S | | 16 | 72 | | 3 | | | | | | Al = 5, Mn = 4 |
| Gemini-II | | 12 | 81 | | 2 | | | | | | Al = 3, Be = 2 |
| KIK | | | | | | | | 87.0 | 4.0 | 8.0 | Ag = 1.0 |

In the present invention, a bonding agent is used as a primer for aiding the formation of the thermally sprayed layer comprising predominantly ceramics. The bonding agent may be self-bonding type materials which can microscopically bond even onto a smooth non-porous substrate at moderate substrate temperatures, for example molybdenum, tantalum, niobium, nickel-chromium-aluminum powdery mixture, nickel-aluminum powdery mixture, or the like, preferably nickel-aluminum powdery mixture. The thickness of the layer of bonding agent may vary depending on a kind of bonding agent and a desired bond strength, generally not more than 500 $\mu$, preferably in a range of 50–150 $\mu$.

The ceramics used in the present invention include white or faint yellow materials having a melting point of 1,500° C or higher, for instance, metal oxides, such as aluminum oxide, zirconium oxide, titanium oxide, which are used alone or in a mixture of two or more thereof. The preferred is aluminum oxide, zirconium oxide or a mixture thereof (e.g. a mixture of 10 to 100% by weight of zirconium oxide and 90 to 0% by weight of aluminum oxide). The ceramics may further include content of $Al_2O_3$ and a lower content of $SiO_2$ than the dentin or enamel porcelain and being capable of forming an opaque layer for sheltering the metallic color. The dentin porcelain is usually coated on the opaque layer and can prepare the shape of the tooth and the color of the tooth body.

The method for producing the metal crown used in the present invention is not limited to a specific method but the conventional lost wax casting method is usually used for the production of dental metal crowns. For instance, an alloy useful for casting a dental metal crown is molten by high-frequency heating, subjected to a centrifugal casting, and then trimmed and ground appropriately to give a metal crown. The resulting metal crown is subjected to grit blasting and thereon is formed a coating layer of (a) (i) a bonding agent and (ii) ceramics or a mixture of ceramics and a porcelain, (b) (i) a bonding agent, (ii) a mixture of a bonding agent and ceramics, and (iii) ceramics, and optionally (iv) a mixture of a ceramics and a porcelain, and (c) (i) a bonding agent, (ii) a mixture of bonding agent and a ceramics or a ceramics, and (iii) a mixture of ceramics and a porcelain, by a thermal spray method (i.e. by blowing and laminating thereon the layer-forming material molten or nearly molten by a technique of combustion or with electric energy), preferably by a plasma spray method (i.e. by applying the layer-forming material in the form of a plasma jet of a supersonic electromagnetic fluid having a high temperature obtained by arcing). When a mixture of a bonding agent and ceramics or a mixture of a ceramics and a porcelain is used, the bonding agent is generally contained in a ratio of 50% by weight or less, preferably 5 to 20% by weight, on the basis of the total weight of the mixture of the bonding agent and ceramics, and on the other hand, in the case of the mixture of a ceramic and a porcelain, the mixed ratio is not specified and may be varied in accordance with the desired purposes. The portion being not to be coated, for instance, the innerface of the metal crown, is previously masked by coating with a masking material such as a marking ink or an aluminum-made adhesive tape prior to subjecting it to grit blasting, and the masked metal crown is applied with various porcelains and baked in a vaccum furnace and thereafter the shape of the product is adjusted so as to be compatible with the adjacent teeth. Finally, it is subjected to glaze baking in an air atmosphere. The most suitable porcelain is selected from the conventional opaque, dentin, enamel, or other porcelains for dental uses depending on the utilities of the artificial tooth crown. The baking temperature of the porcelain may vary with the kinds of the materials, but is usually in the range of 800° to 1,100° C. The baking of the porcelain is preferably carried out by heating rapidly at a baking temperature, for example 1,000° C and then cooling rapidly for preventing the deformation of the product due to the sag of the porcelain as small as possible.

According to the present invention, the stress generated in the porcelain fused to metal crown due to the difference in the thermal expansion coefficient between the metal crown and the porcelain can be moderated by the pores included in the thermally sprayed layers, and further, the bonding of the layers can be sufficiently achieved even by a short baking time because the bonding agent and the ceramics are laminated.

The strength of the artificial tooth crown obtained by the present invention is measured by the Spalling test, which is one of thermal shock tests and is carried out by allowing the artificial tooth crown to stand in an electric furnace at a constant temperature for 10 minutes and then dipping the resultant into ice-water, and observing the occurrence of cracking therein.

The present invention is illustrated by the following Examples but is not limited thereto.

EXAMPLE 1

A metal crown is produced from a cobalt-chromium alloy (Nobilium, trade name of Nobilium Co.).

The cobalt-chromium alloy is molten by high frequency heating and subjected to centrifugal casting. The casted product thus obtained is ground to give a metal crown having a weight of about 0.7 g and a thickness of 0.35 to 0.5 mm. The lower half of the outersurface in the lingual side of the metal crown and the whole innersurface of the metal crown are masked with an aluminum adhesive tape and the masked metal crown is subjected to grit blasting (blasting agent: Metcolite VF, trade name of Metco Inc., pressure: 30 psi) with a ventiblast apparatus (mammoth type, made by Metco Inc., England).

Using a plasma spray apparatus (provided with a 6MR-630 type electric power supplier, made by Metco Inc.) argon-hydrogen-plasma jet flame (arc electric current: 500 Amp) is generated, and firstly nickel-aluminum composite powder (Metco Powder No. 450, made by Metco Inc.; a self-bonding type bonding agent) is thermally sprayed onto the metal crown so as to form a layer having a thickness of about 80 $\mu$ on the surface of the metal crown, and secondly aluminum oxide powder (Metco Powder No. 105, made by Metco Inc.) is thermally sprayed so as to form the second layer having a thickness of about 200 $\mu$ in average.

Various porcelains: opaque (No. 533, made by Vita Co.), dentin (VMK 68–549, made by Vita Co.), enamel (No. 559, made by Vita Co.) and translucent (No. 561, made by Vita Co.) are, in order, applied onto the metal crown obtained above so as to harmonize with adjacent natural teeth. The metal crown thus treated is baked by heating rapidly at 1,000° C in a vacuum furnace (excepting the final step of glaze baking) and then cooling rapidly. The final glaze baking step is carried out by heating rapidly at 1,000° C and then cooling rapidly under the atmosphere of air to give an artificial tooth crown.

The artificial tooth crown thus obtained was inserted into the oral cavity of human and kept for 6 months. As the result, the artificial tooth crown could satisfactorily be used without any breaking, any change in color and any injurious effect on the tissues around the tooth.

Besides, the artificial tooth crown obtained in the same manner as described above was subjected to Spalling test, but no change of the tooth crown was observed at 400° C. Moreover, the artificial tooth crown showed a breaking strength of 120 kg, which was measured by a compression tester.

EXAMPLE 2

A metal crown is produced from a cobalt-chromium alloy (Nobilium, trade name of Nobilium Co.) and then is subjected to masking and grit blasting in the same manner as described in Example 1.

Using a plasma spray apparatus (provided with a 6MR-630 type electric power supplier, made by Metco Inc.) argon-hydrogen-plasma jet flame (arc electric current: 500 Amp) is generated, and firstly nickel-aluminum composite powder (No. 450, made by Metco Inc.; a self-bonding type bonding agent) is thermally sprayed onto the metal crown so as to form a layer having a thickness of about 80 $\mu$ on the surface of the metal crown, secondly a mixture of 10% by weight of nickel-aluminum composite powder and 90% by weight of zirconium oxide (Metco Powder No. 201, made by Metco Inc.) is thermally sprayed so as to form the second layer having a thickness of about 100 $\mu$ in average, and thirdly a powdery mixture of 45% by weight of zirconium oxide, 45% by weight of aluminum oxide (Metco Powder No. 105, made by Metco Inc.) and 10% by weight of dentin porcelain (VMK68-549, made by Vita Co.) is thermally sprayed so as to form the third layer having a thickness of about 100 $\mu$ in average.

For making the color of the artificial tooth similar to the adjacent natural tooth, a further small amount of dentin porcelain is applied. The metal crown thus treated is baked by heating rapidly at 1,000° C in a vacuum furnace and then cooling rapidly. After applying further an enamel porcelain (No. 559, made by Vita Co.) thereto, the resultant is heated rapidly at 1,000° C and then cooled rapidly under the atmosphere of air to give an desired artificial tooth crown.

The artificial tooth crown thus obtained was inserted into the oral cavity of a human and kept for 5 months. As the result, the artificial tooth crown could satisfactorily be used without any breaking and any injurious effect on the tissues around the tooth and in good harmony with the adjacent teeth in the color.

Further, the artificial tooth crown obtained in the same manner as described above was subjected to Spalling test, but no change of the tooth was observed at 430° C.

Another artificial tooth crown, which was obtained in the same manner as described above excepting that the third layer was formed by using a mixture of 50% by weight of zirconium oxide and 50% by weight of aluminum oxide instead of the mixture of 45% by weight of zirconium oxide, 45% by weight of aluminum oxide and 10% by weight of dentin porcelain, was subjected to the Spalling test likewise. As the result, no change of the tooth was observed at 430° C.

EXAMPLE 3

An artificial tooth crown is produced in the same manner as described in Example 1 excepting that a nickel-chromium alloy (Wiron-S, trade name of Bremer Goldschlag Wilh-Herbst) is used as the material for the metal crown instead of the cobalt-chromium alloy.

During the steps for producing the artificial tooth crown, no peeling or cracking of the porcelain layer was observed. Besides, when the artificial tooth crown was subjected to Spalling test at 400° C, no change of the artificial tooth was observed.

On the contrary, when the metal crown produced from the same nickel-chromium alloy as used above was subjected to grit blasting and then applied with opaque, dentin, enamel and translucent porcelains in the same manner as described in Example 1 excepting that the plasma spray treatment was omitted, the artificial tooth crown thus obtained was broken at about 250° C in the Spalling test.

EXAMPLE 4

A metal crown is produced from a gold alloy (KIK, trade name of Ishifuku Kinzoku K.K.) instead of the cobalt-chromium alloy in Example 1 and then is subjected to masking and grit blasting in the same manner as described in Example 1.

Using the same plasma spray apparatus as used in Example 1, argon-hydrogen-plasma jet flame (arc electric current: 500 Amp) is generated, and firstly nickel-aluminum composite powder (a self-bonding type bonding agent) is thermally sprayed onto the metal crown so as to form a layer having a thickness of about 80 μ on the surface of the metal crown, and secondly a powder of zirconium oxide (100% by weight) is thermally sprayed so as to form the second layer having a thickness of about 200 μ in average.

The metal crown thus treated is further treated in the same manner as described in Example 2 to give the desired artificial tooth crown.

During the steps for producing the artificial tooth crown, no peeling or cracking of the porcelain layer was observed. Besides, when the artificial tooth crown was subjected to Spalling test at 400° C, no change of the artificial tooth was observed.

Although any opaque porcelain is not used, the golden color is completely sheltered and the color of the artificial tooth crown is well harmonized with the color of the adjacent natural teeth when it is inserted into the oral cavity of human.

For comparison purposes, a conventional porcelain fused to metal crown (artificial tooth crown) is prepared by subjecting a metal crown made from the same gold alloy as used above to the treatment with hydrofluoric acid and the degassing treatment, applying thereto opaque, dentin and enamel porcelains and then subjecting the resultant to baking. When the artificial tooth crown was subjected to the Spalling test, it was broken at about 250° C.

Moreover, when the breaking strength of these artificial tooth crowns was measured by a compression tester, the breaking strength of the artificial tooth crown of the present invention was 45 kg, and that of the conventional artificial tooth crown was 30 kg.

EXAMPLE 5

A metal crown is produced from a gold alloy (KIK, trade name of Ishifuku Kinzoku K.K.) and then is subjected to masking and grit blasting in the same manner as described in Example 1.

In the same manner as described in Example 1 using the same plasma spray apparatus, firstly a nickel-aluminum composite powder is thermally sprayed onto the metal crown so as to form a layer having a thickness of about 80 μ on the surface thereof, secondly zirconium oxide (100% by weight) is thermally sprayed so as to form the second layer having a thickness of about 150 μ, thirdly a mixture of 25% by weight of zirconium oxide, 25% by weight of aluminum oxide and 50% by weight of dentin porcelain (Aluminous Porcelain S-D-25, trade name of Columbus Co.) is thermally sprayed so as to form the third layer having a thickness of 200 μ in minimum and 1.5 mm in maximum, and the shape of the crown is modified with a diamond point, and then fourthly an enamel porcelain is applied.

The metal crown thus treated is baked in the same manner as described in Example 1 to give the desired artificial tooth.

The artificial tooth crown thus obtained has a good color and the shape thereof is easily modified by cutting. Furthermore, no cracking or breaking of the porcelain layer was observed during the steps of the production thereof, and no change of the artificial tooth was observed in the Spalling test at 400° C.

As is explained above, while it has been considered that the fusing of the porcelain onto the metal crown is very difficult, according to the present invention, the fusing of the porcelain onto the metal crown can be practically easily done by forming the plasma spray layer of ceramics around the metal crown and there can be obtained the desired artificial tooth crown having an excellent strength and being also excellent from the esthetic viewpoint.

Besides, when the plasma spray layer of the ceramic comprising predominantly zirconium oxide is formed around the metal crown, the desired artificial tooth crown having an excellent strength and having the color similar to that of natural teeth can be obtained within a comparatively short time without using any opaque porcelain. When the spray layer of a mixture of ceramics and porcelains is formed, it is not required to apply various porcelains, but the mere application of an enamel porcelain can give the desired artificial tooth crown, and the shape of product can easily be modified by cutting.

Moreover, according to the present invention, because the laminated spray layers including pores are formed between the metal crown and the porcelain layer, the distortion of the porcelain fused to metal crown due to the difference in the thermal expansion coefficient between the metal crown and the porcelain can be moderated, and further, the compatibility of the metal crown with the porcelain is good and the artificial tooth crown have superior breaking strength in comparison with the conventional artificial tooth crown made from, for example, a gold-palladium-platinum alloy (KIK, trade name of Ishifuku Kinzoku K.K.).

What is claimed is:

1. A porcelain fused to metal crown having a composite structure comprising layers of a bonding agent and ceramics which are thermally sprayed around the metal crown, and a layer of fused porcelain formed on the above layers.

2. The porcelain fused to metal crown according to claim 1, wherein the thermally sprayed layer of the ceramics is that of aluminum oxide.

3. The porcelain fused to metal crown according to claim 1, wherein the thermally sprayed layer of the ceramics is that of zirconium oxide or a mixture of zirconium oxide and aluminum oxide.

4. A porcelain fused to metal crown having a composite structure comprising layers of a bonding agent, a mixture of a bonding agent and ceramics, ceramics, and optionally a mixture of a ceramics and a porcelain, which are thermally sprayed around the metal crown, and a layer of fused porcelain formed on the above layers.

5. A porcelain fused to metal crown having a composite structure comprising layers of a bonding agent, a mixture of a bonding agent and ceramics or ceramics and a mixture of ceramics and a porcelain, and a layer of fused porcelain formed on the above layers.

6. A process for producing a porcelain fused to metal crown, which comprises producing a metal crown by casting a dental casting alloy, thermally spraying thereon a bonding agent and ceramics to form layers of the bonding agent and the ceramics, and fusing thereon a porcelain to form a layer of fused porcelain.

7. A process for producing a porcelain fused to metal crown, which comprises producing a metal crown by casting a dental casting alloy, thermally spraying thereon a bonding agent, a mixture of a bonding agent and ceramics, and ceramics, and optionally a mixture of ceramics and porcelain, in order, to form layers thereof, and fusing thereon a porcelain to form a layer of fused porcelain.

8. A process for producing a porcelain fused to metal crown, which comprises producing a metal crown by casting a dental casting alloy, thermally spraying thereon a bonding agent, a mixture of a bonding agent and ceramics or ceramics and a mixture of a ceramics and a porcelain, in order, to form layers thereof, and fusing thereon a porcelain to form a layer of fused porcelain.

9. A porcelain fused to a metal crown having a composite structure comprising layers of a bonding agent, a mixture of a bonding agent and zirconium oxide ceramics and a layer of a ceramic mixture of 10 to 100% by weight of zirconium oxide and 90 to 0% by weight of aluminum oxide, and optionally a mixture of a ceramic and porcelain, which are thermally sprayed on the metal crown, and a layer of fused porcelain formed on the above layers.

10. A porcelain fused to a metal crown having a composite structure comprising layers of a bonding agent, a mixture of a bonding agent and a ceramic or zirconium oxide ceramic and a mixtuee of zirconium oxide and aluminum oxide ceramics with a porcelain, and a layer of fused porcelain formed on the above layers.

11. A porcelain fused metallic tooth crown comprising a metallic tooth crown base made of a dental casting alloy, a thermally sprayed layer of a bonding agent selected from the group consisting of molybdenum, tantalum, niobium, a nickel-chromium-aluminum powdery mixture, and a nickel-aluminum powdery mixture which is formed around the metallic tooth crown base, a thermally sprayed layer of ceramics selected from the group consisting of aluminum oxide, zirconium oxide, titanium oxide and a mixture thereof which is formed or said layer of a bonding agent, and a surface layer of fused porcelain.

12. A porcelain fused metallic tooth crown comprising a metallic tooth crown base made of a dental casting alloy, a thermally sprayed layer of a bonding agent formed around the metallic tooth crown base, a thermally sprayed layer of a mixture of a bonding agent, a thermally sprayed layer of ceramics formed on the layer of a mixture of a bonding agent and ceramics, a surface layer of fused porcelain, and optionally a thermally sprayed layer of ceramics and porcelain which may exist between the layer of ceramics and the sueface layer of fused porcelain, said bonding agent being selected from the group consisting of molybdenum, tantalum, niobium, a nickel-chormium-aluminum powdery mixture and a nickel-aluminum powdery mixture, and said ceramics selected from the group consisting of aluminum oxide, zirconium oxide, titanium oxide, and a mixture thereof.

13. A porcelain-fused metallic tooth crown comprising a metallic tooth crown base made of a dental caating alloy, a thermally sprayed layer of a bonding agent formed around the metallic tooth crown base, a thermally sprayed layer of a mixture of a bonding agent and ceramics formed on the layer of a bonding agent, a thermally sprayed layer of ceramics formed on the layer of a bonding agent and ceramics, a thermally sprayed layer of a mixture of ceramics and porcelain formed on the layer of ceramics, and a surface layer of fused porcelain, said bonding agent being selected from the group consisting of molybdenum, tantalum, niobium, a nickel-chromium-aluminum powdery mixture, and a nickel-aluminum powdery mixture, and said ceramics selected from the group consisting of aluminum oxide, zirconium oxide, titanium oxide and a mixture thereof.

* * * * *